United States Patent [19]

Kawashima

[11] Patent Number: 5,510,520
[45] Date of Patent: Apr. 23, 1996

[54] OPTICAL RESOLUTION METHOD

[75] Inventor: Masatoshi Kawashima, Yokohama, Japan

[73] Assignee: Kankyo Kagaku Center Co., Ltd., Kanagawa, Japan

[21] Appl. No.: 293,036

[22] Filed: Aug. 19, 1994

Related U.S. Application Data

[63] Continuation of Ser. No. 974,826, Nov. 16, 1992, Pat. No. 5,395,962, which is a continuation of Ser. No. 739,314, Aug. 1, 1991, abandoned.

[30] Foreign Application Priority Data

| | | | |
|---|---|---|---|
| Aug. 6, 1990 | [JP] | Japan | 2-206846 |
| Sep. 14, 1990 | [JP] | Japan | 2-242706 |
| Dec. 27, 1990 | [JP] | Japan | 2-414693 |
| Apr. 23, 1991 | [JP] | Japan | 3-117859 |

[51] Int. Cl.$^6$ ................................................ C07D 227/06
[52] U.S. Cl. .................... 562/401; 562/402; 568/735; 560/56
[58] Field of Search .............. 560/56; 562/401g300201; 568/735

[56] References Cited

U.S. PATENT DOCUMENTS 4,401,820  8/1983  Chibata et al. .................... 562/401

OTHER PUBLICATIONS

Kawashima et al., Chemistry Letters, No. 12, Dec. 1990, pp. 2299–2300.
Kawashima et al., Chemistry Letters, No. 5, May 1991, pp. 763–766.
Toda et al., The Journal of Organic Chemistry, vol. 53, No. 15, 22nd Jul. 1988, pp. 3607–3609.
Toda et al., Tetrahedron Letters, vol. 29, No. 15, 1988, pp. 1807–1810.
Toda et al., Tetrahedron Letters, vol. 25, No. 43, 1984, pp. 4929–4932.
Tamai et al., Synthesis, No. 3, Mar. 1990, pp. 222–223.
Hutchins et al., The Journal of Organic Chemistry, vol. 45, No. 12, 6th Jun. 1980, pp. 2414–2418.
Muriel et al, Journal of the Chemical Society, 1955, pp. 1242–1251.

*Primary Examiner*—Marianne M. Cintins
*Assistant Examiner*—Keith MacMillan
*Attorney, Agent, or Firm*—Wenderoth, Lind & Ponack

[57] ABSTRACT

The present invention provides three optical resolution methods. The first aspect comprises the steps of adding an optically active bifunctional resolving reagent to a bifunctional compound to form a liquid material, precipitating crystals therefrom, and treating the crystals and the liquid material separately with an acidic material, a basic material, or a basic material and an acidic material, to obtain a pair of enantiomers of an optically active bifunctional compound. The second aspect comprises an optical resolution method by which one necessary enantiomer of a pair of enantiomers in an optically active bifunctional compound is exclusively obtained. The third aspect comprises a method for racemizing one unnecessary enantiomer of a pair of enantiomers in an optically active bifunctional compound which is formed by the optical resolution method of the present invention.

5 Claims, No Drawings

OPTICAL RESOLUTION METHOD

This is a continuation application of Ser. No. 07/974,826 filed Nov. 16, 1992, now U.S. Pat. No. 5,395,962, which is a continuation of now abandoned application Ser. No. 07/739,314 filed Aug. 1, 1991 now abandoned.

BACKGROUND OF THE INVENTION (i) Field of the Invention

The present invention relates to an optical resolution method of functional compounds and a racemization method of optically active bifunctional compounds.

(ii) Description of Related Art

Bifunctional compounds such as diols, dihydroxybiaryls and hydroxyoximes are neutral or slightly acidic, and therefore they do not usually interact on a resolving reagent, when they are intactly present without any additional treatment. Furthermore, each of these compounds has plural functional groups, and for this reason, it is extremely difficult to resolve them. Conventional optical resolution methods of which there are only a small number comprise converting the bifunctional compound into a derivative such as an ester, and then resolving it, and resolving reagents which are used in these methods are not easily available. In consequence, these conventional methods are not practical.

For example, as a purely chemical optical resolution method, there is known a process which comprises resolving, with cinchonine or cinchonidine, a phosphate obtained by reacting racemic 2,2'-dihydroxy-1,1'-binaphthyl with phosphorus oxychloride [Org. Synth., 67, 1 (1988)], or resolving the same with optically active 2-aminobutanol (Synthesis, 222 (1990), and then reducing with lithium aluminum hydride [Org. Synth., 67, 13 (1988)] to obtain optically active 2,2'-dihydroxy-1,1'-binaphthyl. However, this process requires the complicated operation of converting 2,2'-dihydroxy-1,1'-binaphthyl into the phosphate, optically resolving the same, and then removing a phosphoric acid portion therefrom by the reduction, and in the last step of this process, phosphine which is a poisonous gas is produced which is inconvenient.

Moreover, in the conventional optical resolution methods, the necessary enantiomer of the optically active compound is used and removed from a pair of enantiomers, and the remaining unnecessary enantiomer is useless and uneconomical. Accordingly, it is important how the unnecessary enantiomer is effectively racemized and then returned to the necessary enantiomer. However, the racemization of optically active binaphthols has scarcely been researched, and only methods of reacting with hydrochloric acid in dioxane and other methods of reacting with potassium hydroxide in butanol are known.

In these methods, however, the racemization is slow and volumetric efficiency is also low. Therefore, there are desired a racemization method of optically active binaphthols which permits the racemization to proceed rapidly and which is excellent in volumetric efficiency and is economical, a racemization method which does not require any especial racemization step, and an optical resolution method which permits obtaining a necessary enantiomer.

SUMMARY OF THE INVENTION

The present invention intends to solve the above-mentioned problems, and the first object of the present invention is to provide an optical resolution method of a bifunctional compound which is easy and which is industrially practical and safe.

The second object of the present invention is to provide an optical resolution method by which one necessary enantiomer of a pair of enantiomers in an optically active bifunctional compound is exclusively obtained.

The third object of the present invention is to provide a method for racemizing one unnecessary enantiomer of a pair of enantiomers in an optically active bifunctional compound which is formed by the optical resolution method of the present invention.

The optical resolution method of a bifunctional compound according to the present invention is characterized by reacting an optically active bifunctional resolving reagent with the bifunctional compound.

The optical resolution method of the present invention include the following three aspects.

The first aspect comprises the steps of adding an optically active bifunctional resolving reagent to a bifunctional compound to form a liquid material, precipitating crystals therefrom, and treating the crystals and the liquid material separately with an acidic material, a basic material, or a basic material and an acidic material, to obtain a pair of enantiomers of an optically active bifunctional compound.

The second aspect comprises the steps of adding an optically active bifunctional resolving reagent to a bifunctional compound to form a liquid material, precipitating crystals therefrom, separating the crystals from the liquid material, (a) treating the crystals with an acidic material, a basic material, or both a basic material and an acidic material, (b) heating the liquid material, cooling it or allowing it to stand, whereby crystals are formed, and then treating the crystals with an acidic material, a basic material, or both a basic material and an acidic material, and then collecting one enantiomer alone of a pair of enantiomers of an optically active bifunctional compound from the above-mentioned steps (a) and (b).

The third aspect comprises the steps of adding an optically active bifunctional resolving reagent to a bifunctional compound to form a liquid material, precipitating crystals therefrom, separating the crystals from the liquid material, (a) heating the crystals or treating the same with an acidic material, a basic material, or both a basic material and an acidic material, and then adding an optically inactive diamine thereto to form a racemic bifunctional compound, (b) treating the liquid material with an acidic material, a basic material, or both a basic material and an acidic material, and then collecting only one enantiomer of an optically active bifunctional compound obtained in the above-mentioned step (b).

Furthermore, the racemization method of an optically active bifunctional compound according to the present invention comprises heating an optically active bifunctional compound or both an optically active bifunctional compound and an optically inactive diamine, or adding a solvent thereto and then heating them, or only adding a solvent thereto, whereby a liquid product is formed.

DESCRIPTION OF THE PREFERRED EMBODIMENTS

In an optical resolution method of the present invention, a bifunctional compound and an optically active bifunctional compound are preferably similar to each other in structural symmetry, and more preferably they are the same in this point.

The functional groups of the bifunctional compound which is used in the present invention are the identical or different groups selected from the group consisting of a hydroxyl group, amino group, imino group, carboxyl group, hydroxyimino group, hydroxyaryl group and mercapto group.

The bifunctional compound is a compound represented by the formula (A)

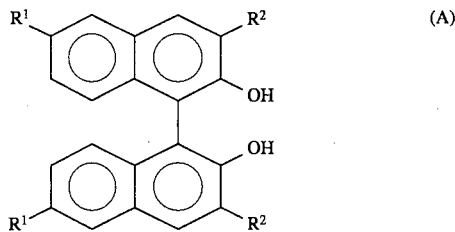

wherein $R^1$ is H, Br or OH, and $R^2$ is H, Br, OH, $CH_3$, $CO_2H$, $CO_2CH_3$, $CO_2CH_2CH_3$ or $CH_2OH$.

Typical examples of the bifunctional compound include binaphthols such as 2,2'-dihydroxy-1,1'-binaphthyl, 6,6'-dibromo-2'2-dihydroxy-1,1'-binaphthyl, 2,2'-dihydroxy-3,3'-bismethoxycarbonyl-1,1'-binaphthyl, 2,2'-dihydroxy-3,3'-bishydroxymethyl-1,1'-binaphthyl, 2,2'-dihydroxy-3,3'-dimethyl-1,1'-binaphthyl, 2,2',6,6'-tetrahydroxy-1,1-binaphthyl and 2,2',3,3'-tetrahydroxy-1,1'-binaphthyl; diol compounds such as 1,2-butanediol, 1,3-butanediol, 2,3-butanediol, 3,4-hexanediol, 4,5-octanediol, 5,6-decanediol, 1,2-cyclopentanediol, 1,2-cyclohexanediol, 1,2-cyclooctanediol, 1,2-diphenyl-1,2-ethanediol and 1,2-dihydro-1,2-dihydroxybenzene; a dihydroxybiaryl compound such as 6,6'-dimethyl-2,2'-dihydroxy-1,1'-biphenyl; hydroxyoxime compounds such as 2-hydroxy-3-hydroxyiminobutane, 3-hydroxy-4-hydroxyiminohexane, 4-hydroxy-5-hydroxyiminooctane, 5-hydroxy-6-hydroxyiminodecane, 1,2-diphenyl-1-hydroxy-2-hydroxyiminoethane and 1,2-bis(4-methoxyphenyl)-1-hydroxy-2-hydroxyiminoethane; dicarboxylic acids such as 2,3-dimethylsuccinic acid and 2,3-diphenylsuccinic acid; and diamino compounds such as 1,2-diaminopropane, 2,3-diaminobutane, 1,2-cyclohexanediamine, 1,2-diphenylethylenediamine, 2,2'-diamino-1,1'-binaphthyl. These compounds may be racemic modifications or partially resolved compounds of the racemic modifications.

Examples of an optically active bifunctional resolving reagent which can be used in the present invention include optically active compounds such as 1,2-diaminopropane, 2,3-diaminobutane, 1,2-cyclohexanediamine, 1,2-diphenylethylenediamine and 2,2'-diamino-1,1'-binaphthyl.

Examples of a solvent which can be used in the resolution method of the present invention usually include aromatic hydrocarbons such as benzene, toluene, xylene, chlorobenzene and bromobenzene: ethers such as diethyl ether, tetrahydrofuran and dioxane; aliphatic hydrocarbons such as pentane and hexane; alcohols such as methanol and ethanol; acetonitrile; and mixed solvents of two or more thereof.

The amount of the resolving reagent is usually from 0.5 to 1.5 equivalents, preferably 1 equivalent to the bifunctional compound. When the amount of the resolving reagent is less than 0.5 equivalent or more than 1.5 equivalents, this reagent sometimes has an influence on chemical yield and optical purity.

Two kinds of complex compounds can be produced from the resolving reagent and the functional compound, and they are different from each other in crystallinity and solubility, with the result that they can be separated into crystals and a liquid material easily by means of filtration or chromatography. Furthermore, the crystals can be more purified by recrystallization. These two kinds of complex compounds are considered to be diastereometic compounds.

In the optical resolution method of the present invention, as a process of mixing the bifunctional compound with the optically active bifunctional resolving reagent to form a liquid material and then precipitating crystals, there can be employed a process comprising the steps of the addition of a solvent, heating, dissolving and then cooling; a process comprising the steps of heating and then cooling; a process comprising the steps of the addition of a solvent and then standing; or a process comprising the steps of mixing and then standing. The thus obtained crystals are separated from the liquid material by filtration or centrifugal separation. The crystals and the liquid material which are obtained by the separation can be treated with an acidic material, a basic material, or both a basic material and an acidic material in accordance with the selected bifunctional compound. This treatment brings about decomposition, and the optically active bifunctional compound is then separated from the resolving reagent.

Typical examples of the acidic material include hydrochloric acid, sulfuric acid, acetic acid, phenol, cresol, naphthol, binaphthol and silica gel. Typical examples of the basic material include sodium hydroxide, potassium hydroxide, triethylamine and alumina.

The treatment can proceed in accordance with any one of the following processes (1), (2) and (3).

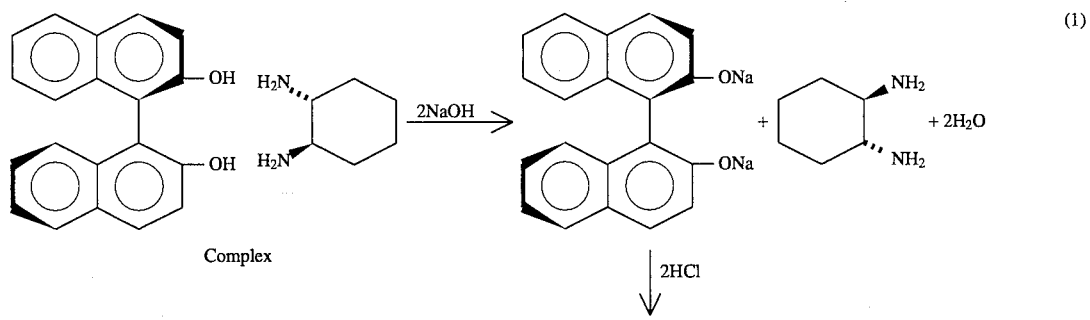

(1)

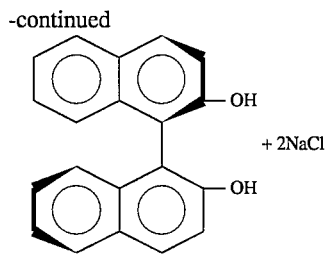

(2)

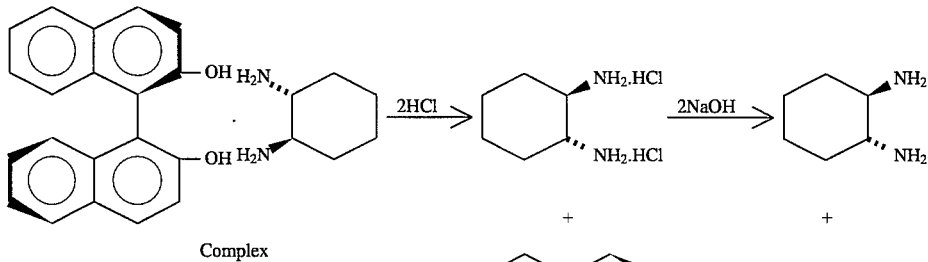

(3)

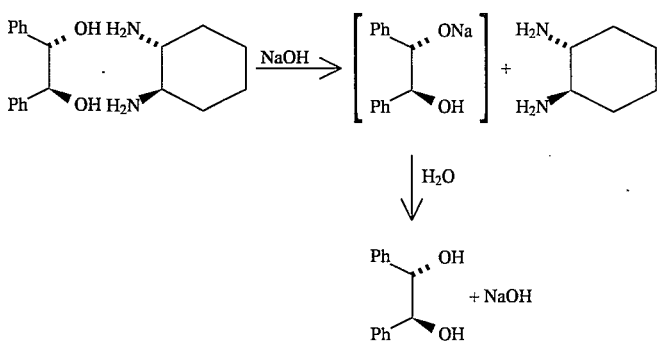

In case that the basic material is used, a treatment temperature is in the range of from −10° to +100° C., and in case that the acidic material is used, it is in the range of from −10° to +100° C. In both cases, the treatment temperature is preferably from 0° to +30° C.

An optical resolution method regarding the first aspect of the present invention is, for example, as follows.

A bifunctional compound which is a racemic modification or a partially resolved compound is reacted with 0.5 to 1.5 equivalents of an optically active bifunctional resolving reagent in a solvent such as benzene, and the precipitated crystals are then separated from the solution. The separated crystals are purified by recrystallization from a solvent such as benzene, if necessary. When the recrystallization is repeated, the crystals having an optical after high extremely high purity can be obtained. The thus obtained crystals are treated with a mineral acid or the like, and the liberated and optically active bifunctional compound is collected by filtration or extracted with an organic solvent, washed with water, and then dried, or alternatively this compound is passed through a silica gel column chromatography and then eluted with an organic solvent, thereby obtaining an optically active bifunctional compound.

Furthermore, the filtrate separated from the crystals is concentrated and then treated with a mineral acid to obtain an enantiomer of the above-mentioned optically active bifunctional compound obtained by treating the crystals. This enantiomer is reacted with an enantiomer of the initially used resolving reagent to form crystals, and the crystals are then treated by the same procedure as in the previous paragraph, whereby optical purity can be heightened.

The crystals are treated with an acid, and the resolving reagent present in the filtrate from which the bifunctional compound has been removed is then treated with an alkali, so that the resolving reagent is recovered in a high yield without lowering the optical purity.

Moreover, in the present invention, the optically active compound can be obtained by exchanging the functions of the bifunctional compound and the resolving reagent. For example, a racemic diamino compound is optically resolved with an optically active diol compound to obtain an optically active diamino compound (Examples 23 and 24).

The optical resolution method of the present invention will be described in more detail, where 2,2'-dihydroxy-1,1'-binaphthyl represented by the formula

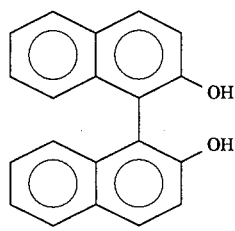 (I)

is used as the bifunctional compound and optically active 1,2-diphenylethylenediamine represented by the formula

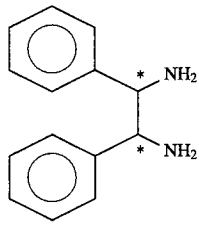 (II)

is used as the optically active bifunctional resolving reagent.

In one embodiment, 2,2'-dihydroxy-1,1'-binaphthyl represented by the formula (I) is reacted with (1R,2R)-(+)-1,2-diphenylethylenediamine represented by the formula

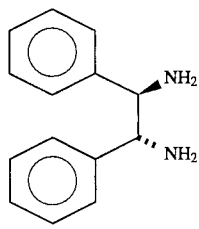 (II$_R$)

to form a complex, and this complex is then treated with a mineral acid, thereby obtaining (R)-(+)-2,2'-dihydroxy-1,1'-binaphthyl represented by the formula

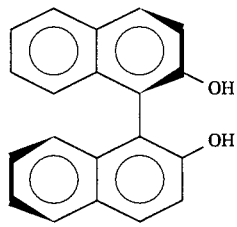 (I$_R$)

In another embodiment, 2,2'-dihydroxy-1,1'-binaphthyl represented by the formula (I) is reacted with (1S,2S)-(−)-1,2-diphenylethylenediamine represented by the formula

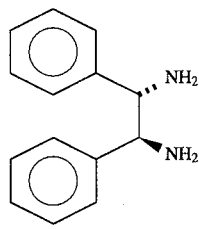 (II$_S$)

to form a complex, and this complex is then treated with a mineral acid, thereby obtaining (S)-(−)-2,2'-dihydroxy-1,1'-binaphthyl represented by the formula

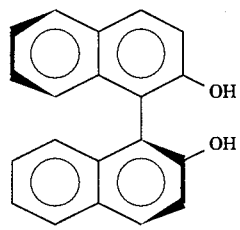 (I$_S$)

Examples of the optically active 1,2-diphenylethylenediamine represented by the formula (II) are optically active threo-1,2-diphenylethylenediamines such as (1R,2R)-(+)-1,2-diphenylethylenediamine of the formula (II$_R$) and (1S,2S)-(−)-1,2-diphenylethylenediamine of the formula (II$_S$). One of these diamines can be used in compliance with the intended purpose.

The amount of the optically active diamine is from 0.5 to 1.0 equivalent to 2,2'-dihydroxy-1,1'-binaphthyl. When this amount is less than 0.5 equivalent, the yield of the product lowers, and when it is more than 1.0 equivalent, the yield and optical purity are not affected but such a usage is not economical. Optically active 1,2-diphenylethylenediamine for 2,2'-dihydroxy-1,1'-binaphthyl dissolves in a solvent and functions to form a sparingly soluble complex.

Usable examples of the mineral acid include hydrochloric acid and sulfuric acid, and the amount of the mineral acid is more than the equivalent of optically active 1,2-diphenylethylenediamine to be used. The mineral acid is usually used in the state of an aqueous solution or a mixed solution containing water and an alcohol, and no restriction is put on the concentration of the mineral acid but a range of from 0.1 to 1M is preferable. In the case of the aqueous alcohol solution, the concentration of the alcohol is preferably 50% or less so that 2,2'-dihydroxy-1,1'-binaphthyl may easily precipitate.

Usable examples of the solvent include aromatic hydrocarbons such as benzene and toluene, and a mixed solvent of the aromatic hydrocarbon and an aliphatic hydrocarbon such as hexane.

A temperature for the treatment of the complex with the mineral acid is usually from 0° to 30° C., preferably 0° to 15° C.

The concrete procedures of the above methods are as follows.

Racemic 2,2'-dihydroxy-1,1'-binaphthyl and 0.5 to 1.5 equivalents of optically active 1,2-diphenylethylenediamine are added to a solvent such as benzene, and they are heated, dissolved in the solvent, and then cooled to form a supersaturated solution, and the precipitated sparingly soluble complex is separated from the solution. Alternatively, a benzene solution containing 0.5 to 1.5 equivalents of optically active 1,2-diphenylethylenediamine is added to a benzene solution of racemic 2,2'-dihydroxy-1,1'-binaphthyl, and the precipitated sparingly soluble complex is separated from the solution.

The thus obtained complex is purified by recrystallization from a solvent such as benzene, if necessary. Afterward, this complex is treated with a mineral acid, so that optically active 2,2'-dihydroxy-1,1'-binaphthyl is liberated in the state of a white solid. This solid is collected by filtration, washed with water, and then dried to obtain optically active (R)-(+)-2,2'-dihydroxy-1,1'-binaphthyl or (S)-(−)-2,2'-dihydroxy-1,1'-binaphthyl.

A filtrate separated from the sparingly soluble complex is concentrated to obtain a readily soluble complex, and this complex is then treated with a mineral acid to obtain optically active 2,2'-dihydroxy-1,1'-binaphthyl having a steric configuration opposite to that of optically active 2,2'-dihydroxy-1,1'-binaphthyl produced from the sparingly soluble complex. The thus obtained product is further led to the sparingly soluble complex and then subjected to the same treatment as mentioned above to heighten the optical purity.

On the other hand, optically active 1,2-diphenylethylenediamine which is present as a mineral acid salt in the aqueous solution is recovered in a high yield by an alkaline treatment without lowering the optical purity. The thus recovered product can be reutilized as the resolving reagent.

The formed sparingly soluble complex is (R)-(+)-2,2'-dihydroxy-1,1' -binaphthyl•(1R,2R)-(+)-1,2-diphenylethylenediamine complex or (S)-(−)-2,2'-dihydroxy-1,1'-binaphthyl•(1S,2S)-(−)-1,2-diphenylethylenediamine complex. This complex is treated with a mineral acid to hydrolyze itself, so that (R)-(+)-2,2'-dihydroxy-1,1'-binaphthyl or (S)-(−)-2,2'-dihydroxy-1,1'-binaphthyl is liberated.

Even if the 1,2-diphenylethylenediamine represented by the formula (II) is replaced with optically active 1,2-cyclohexanediamine represented by the formula

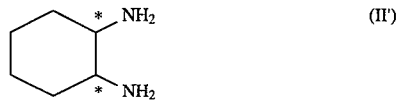

optically active 1,1'-bi-2-naphthol represented by the formula ($I_R$) or the formula ($I_S$) can be obtained as described above.

In one embodiment, 2,2'-dihydroxy-1,1'-binaphthyl represented by the formula (I) is reacted with (1R,2R)-(−)-1,2-cyclohexanediamine represented by the formula

to form a sparingly soluble complex, and this complex is then treated with a mineral acid to obtain (R)-(+)-2,2'-dihydroxy-1,1'-binaphthyl having the formula ($I_R$).

In another embodiment, 2,2'-dihydroxy-1,1'-binaphthyl represented by the formula (I) is reacted with (1S,2S)-(+)-1,2-cyclohexanediamine represented by the formula

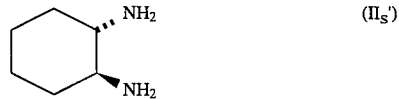

to form a sparingly soluble complex, and this complex is then treated with a mineral acid to obtain (S)-(−)-2,2'-dihydroxy-1,1'-binaphthyl having the formula ($I_S$). In this case, the detailed procedure is the same as mentioned above.

The sparingly soluble complex which can be formed from the solvent containing an aromatic hydrocarbon by the above-mentioned procedure is (R)-(+)-2,2'-dihydroxy-1,1' -binaphthyl•(1R,2R)-(−)-1,2-diaminocyclohexane•benzene (1:1:n) complex or (S)-(−)-2,2'-dihydroxy-1,1'-binaphthyl•(1S,2S)-(+)-1,2 -diaminocyclohexane•aromatic hydrocarbon (1:1:n) complex. This complex is heated up to a temperature which is more than the melting point of the aromatic hydrocarbon contained therein to release the aromatic hydrocarbon therefrom and to thereby obtain (R)-(+)-2,2' -dihydroxy-1,1'-binaphthyl•(1R,2R)-(−)-1,2-diaminocyclohexane (1:1) complex or (S)-(−)-2,2'-dihydroxy-1,1'-binaphthyl•(1S,2S)-(+)-1,2-diaminocyclohexane (1:1) complex. Here, when the aromatic hydrocarbon is benzene, n is 2; when it is toluene, n is 1; and when it is xylene, n is 0.5. Furthermore, the complex formed from the solvent containing no aromatic hydrocarbon is (R)-(+)-2,2'-dihydroxy-1,1'-binaphthyl•(1R,2R)-(−)-1,2-diaminocyclohexane (1:1) complex or (S)-(−)-2,2'-dihydroxy-1,1'-binaphthyl•(1S,2S)-(+)-1,2-diaminocyclohexane (1:1) complex.

Each sparingly soluble complex is treated with a mineral acid to hydrolyze itself, so that (R)-(+)-2,2'-dihydroxy-1,1'-binaphthyl or (S)-(−)-2,2'-dihydroxy-1,1'-binaphthyl is liberated.

The second aspect of the optical resolution method of the present invention is directed to a method which comprises the steps of subjecting the liquid product obtained in the first aspect to an additional crystallization treatment, and then treating the resultant crystals in the same manner as in the first aspect to obtain an optically active bifunctional compound having the same steric configuration as in the enantiomer obtained from the crystals of the first aspect. The above-mentioned crystallization and the treatment of the crystals are identical with those of the first aspect.

The second aspect of the optical resolution method of the present invention comprises the steps of adding an optically active bifunctional resolving reagent to a bifunctional compound to form a liquid material, precipitating crystals therefrom, separating the crystals from the liquid material, (a) treating the crystals with an acidic material, a basic material, or both a basic material and an acidic material, (b) heating the liquid material, cooling it or allowing it to stand, whereby crystals are formed, and then treating the crystals with an acidic material, a basic material, or both a basic material and an acidic material, and then collecting only one enantiomer of a pair of enantiomers of an optically active bifunctional compound from the above-mentioned steps (a) and (b).

In a more preferable method, a mixture of the bifunctional compound and the optically active bifunctional resolving reagent is freshly added to the liquid material in the above-mentioned step (b) to continuously obtain one compound of enantiomers.

The optical resolution method of the second aspect is, for example, as follows.

A solution of a binaphthol and optically active 1,2-diamine is heated and then allowed to stand, and the resultant crystals are collected by filtration. The filtrate is further heated under reflux and then allowed to stand, and the resultant crystals are collected by filtration. This operation is then repeated.

Suitable examples of the amine to be used include optically active 1,2-cyclohexadiamine and optically active 1,2-diphenylethyldiamine.

The solvent to be used is to which can dissolve the binaphthol and the amine in the heating step, and suitable examples of the solvent include aromatic hydrocarbons such as benzene, toluene, xylene and bromobenzene, and alcohols such as methanol, ethanol and propanol.

The necessary heating time depends upon structures and amounts of the binaphthol and the amine as well as the kind of solvent, and it also depends largely upon the steric configuration and the optical purity of the binaphthol. As the binaphthol to be used contains an unnecessary enantiomer in large quantities, it is required to prolong a reflux time. However, even if the content of the unnecessary enantiomer is 100%, the binaphthol is racemized almost completely by the reflux for about 24 hours, and the necessary enantiomer is resolved. The reflux under heating is preferably carried out in a nitrogen atmosphere to inhibit decomposition reactions and the like. When the reflux of the filtrate and the crystallization are repeated many times, the yield of the necessary enantiomer increases up to nearly 100%, but in practice, if the operation is only repeated 4 times, the yield will be in excess of 90%. Alternatively, in case that the present invention is applied on an industrial scale, the filtrate obtained at the time of the first optical resolution is added to a mixture of the racemic binaphthol and the optically active diamine, and the solution is then refluxed. Afterward, the precipitated crystals are filtered, and the filtrate is added again to the mixture of the racemic binaphthol and the optically active diamine, followed by the same treatment as described above. This operation can be continuously repeated. The thus obtained crystals can be additionally recrystallized from the same solvent to heighten purity. In carrying out the recrystallization to heighten the purity, it is preferable to stop the heating immediately after the dissolution of the crystals and to then start allowing the solution to stand, because the heating of the crystals for a long period of time decreases the purity unexpectedly. The thus obtained crystals are a complex of the optically active binaphthol and the optically active amine. In order to isolate the optically active binaphthol therefrom, an acid such as hydrochloric acid, sulfuric acid or acetic acid is added to the crystals, and the mixture is then stirred at room temperature to separate the amine therefrom.

Examples of the optically inactive diamine which can be used in the racemization method of the present invention include ethylenediamine, o-phenylenediamine, 1,2-cyclohexanediamine and 1,2-diphenylethylenediamine.

The optical resolution method of the present invention is characterized by causing interactions at two positions between the bifunctional compound to be resolved and the optically active bifunctional resolving reagent. These interactions mean various bonds among functional groups of the bifunctional compound and the optically active bifunctional resolving reagent. For example, they are bonds among a hydroxyl group, a hydroxyimino group, a carboxyl group and an amino group. More concretely, there are (a) a hydrogen bond between the hydroxyl group and the amino group, (b) an ionic bond between the hydroxyl group and the amino group, (c) a hydrogen bond between the hydroxyimino group and the amino group, (d) an ionic bond between the hydroxyimino group and the amino group, and (e) an ionic bond between the carboxyl group and the amino group. These bonds are as follows.

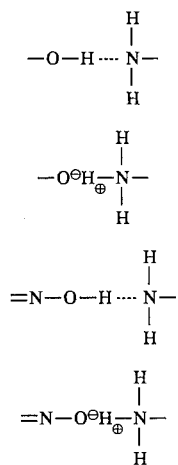

That is, the interactions provide strong hydrogen bonds and ionic bonds, whereby two kinds of compounds are formed which are in a diastereomeric relation and which are largely different from each other in a three dimensional structure and in physical properties such as solubility and the like. Thus, these compounds can be resolved very effectively.

The racemization method of the optically active bifunctional compound according to the present invention comprises heating the optically active bifunctional compound or both the optically active bifunctional compound and the optically inactive diamine; adding a solvent thereto and then heating the mixture; or only adding the solvent thereto to form a liquid substance.

The optically active bifunctional compound which is used in the racemization method of the present invention is preferably an optically active diol compound, more preferably an optically active binaphthol. Typical examples of the optically active binaphthol include compounds represented by the formulae

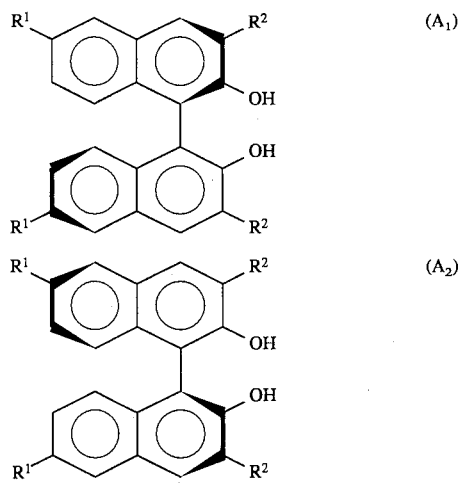

wherein $R^1$ is H, Br or OH, and $R^2$ is H, Br, OH, $CH_3$, $CO_2H$, $CO_2CH_3$, $CO_2CH_2CH_3$ and $CH_2OH$.

In the racemization method of the present invention, the heating operation can be achieved merely by heating the optically active binaphthol to its melting point or more, and a necessary heating time depends upon the structure and amount of the optically active binaphthol but the complete racemization can be accomplished in about 10 minutes after the melting. The racemization is preferably carried out in a nitrogen atmosphere to inhibit decomposition reactions and the like.

In the racemization method of the present invention, the function of the amine is accomplished by heating the optically active binaphthol in the presence of the amine. As the amine to be used, 1,2-diamines such as ethylenediamine, o-phenylenediamine, 1,2-cyclohexanediamine and 1,2-diphenylethylenediamine are desirable from the viewpoint of a racemization rate. When no solvent is used, the racemization can be achieved only by heating the mixture of the above-mentioned materials or the complex previously prepared from the binaphthol and the amine up to its melting point or more. A necessary heating time depends upon the structures and amounts of the binaphthol and the amine but the substantially complete racemization can be attained in about 2 hours after the melting. In order to isolate the racemic binaphthol from the racemized mixture or complex, an acid such as hydrochloric acid, sulfuric acid or acetic acid is added thereto, and the mixture is then stirred at room temperature to separate the binaphthol. When the boiling point of the amine is low, the heating is carried out under reduced pressure, whereby the optically active binaphthol is racemized and simultaneously the amine is separated.

When the racemization is carried out in a solvent, it can be achieved effectively by heating the solution containing the materials up to its boiling point. The solvent to be used is that which can dissolve the optically active binaphthol and the amine in the heating step, and suitable examples of the solvent include benzene, toluene, xylene and bromobenzene. The necessary heating time depends upon structures and amounts of the binaphthol and the amine as well as the kind of solvent, and it also depends largely upon the steric configuration and the optical purity of the binaphthol.

As the binaphthol to be used contains an unnecessary enantiomer in large quantities, it is required to prolong a reflux time. However, even if the content of the unnecessary enantiomer is 100%, the optically active binaphthol is racemized almost completely by the reflux for about 24 hours. The racemization is preferably carried out in a nitrogen atmosphere to inhibit decomposition reactions and the like. In order to isolate the racemic binaphthol from the racemized mixture or the solution of the complex, an acid such as hydrochloric acid, sulfuric acid or acetic acid is added to a residue obtained by distilling off the solvent, and the mixture is then stirred at room temperature to separate the binaphthol. When the boiling point of the amine is low, the residue obtained by distilling off the solvent is heated under reduced pressure, whereby the amine is separated and the racemic binaphthol is obtained.

The third aspect of the present invention is directed to the above-mentioned racemization method of an enantiomer obtained by treating crystals in the first aspect.

According to the optical resolution method of the present invention, the optical resolution of a bifunctional compound can be effectively achieved by the use of an optically active bifunctional resolving reagent. That is, the present invention is a practical optical resolution method for easily resolving a compound whose direct resolution has been before so heretofore so difficult that conversion into a derivative is required. Furthermore, the optical resolution method of the present invention is easy to operate, industrially safe and practical.

Additionally, according to the second and third aspects of the present invention, a necessary enantiomer can be obtained.

The racemization method of the present invention permits easily racemizing an unnecessary compound of a pair of enantiomers of the optically active bifunctional compound and then recovering the racemized compound as the bifunctional compound which is the raw material.

EXAMPLES

Next, the present invention will be described in more detail in reference to examples, but the scope of the present invention should not be limited by these examples.

Example 1

1.28 g (11.2 mmol) of (1R,2R)-(−)-1,2-cyclohexanediamine of $[\alpha]_D^{20}=-36.7°$ (c 4.1, H$_2$O) and 1.00 g (11.1 mmol) of dl-threo-2,3-butanediol were added to 2 ml of ether and then heated/dissolved therein, and the solution was cooled to room temperature. Afterward, the precipitated crystals were collected by filtration and then recrystallized from 2 ml of ether twice to obtain 1.00 g of (1R,2R)-(−)-1,2-cyclohexanediamine•(2R,3R)-(−)-2,3-butanediol. Physical properties of the product are as follows.

m.p. 128°–138° C.

$^1$H-NMR (CDCl$_3$) δ: 1.2 (d, 6H), 2.3 (s, 6H), 0.8–2.7 (m, 10H), 3.3–4.0 (m, 2H)

1.00 g (4.89 mmol) of the above-mentioned crystals was dissolved in ethanol, and the solution was passed through a silica gel short column and then concentrated to obtain 0.428 g (4.75 mmol) of (2R,3R)-(−)-2,3-butanediol.

Yield=86% (to the half amount of dl-threo-2,3-butanediol), and $[\alpha]_D^{20}=-4.8°$ (c 0.3, EtOH).

Example 2

1.00 g (8.76 mmol) of (1R,2R)-(−)-1,2-cyclohexanediamine of $[\alpha]_D^{20}=-36.7°$ (c 4.14, H$_2$O) and 1.02 g (8.78 mmol) of dl-trans-1,2-cyclohexanediol were added to 3 ml of toluene and then heated/dissolved therein, and the solution was cooled to room temperature. Afterward, the precipitated crystals were collected by filtration and then recrystallized from 3 ml of toluene twice to obtain 0.485 g of (1R,2R)-(−)-1,2-cyclohexanediamine•(1R,2R)-(−)-1,2-cyclohexanediol. Physical properties of the product are as follows.

m.p.: 73°–76° C.

IR (cm$^{-1}$, KBr disk): 3450, 3400, 3350, 3600–2400, 1070

$^1$H-NMR (CDCl$_3$) δ: 0.7–2.7 (m, 18H), 2.5 (brs, 6H), 3.1–3.6 (m, 2H)

0.485 g (2.11 mmol) of the above-mentioned crystals was dissolved in ethanol, and the solution was passed through a silica gel short column and then concentrated to obtain 0.245 g (2.11 mmol) of (1R,2R)-(−)-1,2-cyclohexanediol.

Yield=48% (to the half amount of dl-trans-1,2-cyclohexanediol), optical purity=96%, m.p.=98°–100° C., and $[\alpha]_D^{20}=-44.6°$ (c 0.02, H$_2$O).

Example 3

0.268 g (2.35 mmol) of (1R,2R)-(−)-1,2-cyclohexanediamine of $[\alpha]_D^{20}=-36.7°$ (c 4.14, H$_2$O) and 0.502 g (2.34 mmol) of dl-threo-1,2-diphenyl-1,2-ethanediol were added to 10 ml of toluene and then heated/dissolved therein, and the solution was cooled to room temperature. Afterward, the precipitated crystals were collected by filtration and then recrystallized from 5 ml of toluene twice to obtain 0.300 g of (1R,2R)-(−)-1,2-cyclohexanediamine• (1S,2S)-(−)-1,2-diphenyl-1,2-ethanediol. Physical properties of the product are as follows.

m.p.: 95°–98° C.

IR (cm$^{-1}$, KBr disk): 3540, 3440, 3300–2500, 1050

$^1$H-NMR (CDCl$_3$) δ: 0.8–2.7 (m, 10H), 2.6 (s, 6H), 4.6 (s, 2H), 7.1 (s, 10H)

1 ml of methanol and 10 ml of 1M hydrochloric acid were added to 0.300 g (0.913 mmol) of the above-mentioned crystals under ice cooling, followed by stirring for 30 minutes. The solution was extracted with methylene chloride, washed with water, dried over anhydrous sodium sulfate, and then concentrated to obtain 0.193 g (0.901 mmol) of (1S,2S)-(−)-1,2-diphenyl-1,2-ethanediol.

Yield=77% (to the half amount of dl-threo-1,2-diphenyl-1,2-ethanediol), optical purity=98%, and $[\alpha]_D^{24}=-88.3°$ (c 1.25, EtOH).

Example 4

0.826 g (7.23 mmol) of (1R,2R)-(−)-1,2-cyclohexanediamine of $[\alpha]_D^{20}=-36.7°$ (c 4.14, $H_2O$) and 1.04 g (7.21 mmol) of dl-trans-1,2-cyclooctanediol were added to 2 ml of toluene and then heated/dissolved therein, and the solution was cooled to room temperature. Afterward, the precipitated crystals were collected by filtration and then recrystallized from 2 ml of toluene twice to obtain 0.735 g of (1R,2R)-(−)-1,2-cyclohexanediamine•(1R,2R)-(−)-1,2-cyclooctanediol. Physical properties of the product are as follows.

m.p.: 59°–63° C.

IR ($cm^{-1}$, KBr disk): 3450, 3600–2400, 1040

$^1$H-NMR ($CDCl_3$) δ: 0.7–2.7 (m, 22H), 2.2 (brs, 6H), 3.4–3.7 (m, 2H)

0.735 g (2.84 mmol) of the above-mentioned crystals was dissolved in ethanol, and the solution was passed through a silica gel short column and then concentrated to obtain 0.390 g (2.70 mmol) of (1R,2R)-(−)-1,2-cyclooctanediol.

Yield=75% (to the half amount of dl-trans-1,2-cyclooctanediol), and $[\alpha]_D^{24}=-16.4°$ (c 0.32, EtOH).

Example 5

1.00 g (8.76 mmol) of (1R,2R)-(−)-1,2-cyclohexanediamine of $[\alpha]_D^{20}=-35°$ (c 4.00, $H_2O$) and 2.51 g (8.77 mmol) of dl-2,2'-dihydroxy-1,1'-binaphthyl were added to 10 ml of benzene and then heated/dissolved therein, and the solution was cooled to room temperature. Afterward, the precipitated crystals were collected by filtration to obtain 2.05 g (3.68 mmol) of (R)-(+)-2,2'-dihydroxy-1,1'-binaphthyl•(1R,2R)-(−)-1,2-cyclohexanediamine•benzene (1:1:2) complex. Its yield was 84% (to the half amount of dl-2,2'-dihydroxy-1,1'-binaphthyl). Physical properties of the product are as follows.

m.p.: 1 44°–148° C.

$[\alpha]_D^{24}=-16.3°$ (c, 1.02, $CHCl_3$)

IR ($cm^{-1}$, KBr disk): 3450, 3380, 3300, 3060, 2950, 2860, 1620, 1600, 1515, 1460, 1380, 1360, 1230, 1210, 960, 820, 745, 695

$^1$H-NMR ($CDCl_3$) δ: 1.02–2.0 (m, 8H), 3.6 (s, 8H), 7.1–8.3 (m, 12H), 7.4 (s, 12H)

Example 6

5 ml of methanol and. 50 ml of 0.1M hydrochloric acid were added under ice cooling to 2.55 g (4.58 mmol) of (R)-(+)-2,2'-dihydroxy-1,1'-binaphthyl•(1R,2R)-(−)-1,2-cyclohexanediamine•benzene (1:1:2) complex obtained in the same manner as in Example 5, followed by stirring for 30 minutes. The precipitated white solid was washed with water, and then dried under reduced pressure to obtain 1.29 g (4.51 mmol) of (R)-(+)-2,2'-dihydroxy-1,1'-binaphthyl. Yield=98%, optical purity=81% , m.p.=202°–203° C., and $[\alpha]_D^{24}=+29.7°$ (c 0.539, THF).

Example 7

1.79 g (3.22 mmol) of (R)-(+)-2,2'-dihydroxy-1,1'-binaphthyl•(1R,2R)-(−)-1,2 -cyclohexanediamine•benzene (1:1:2) complex obtained in the same manner as in Example 5 was recrystallized from 50 ml of benzene to obtain 1.50 g (2.69 mmol) of colorless transparent needle crystals. This crystalline complex was then decomposed in the same manner as in Example 6 to obtain 0.764 g (2.67 mmol) of (R)-(+)-2,2'-dihydroxy-1,1'-binaphthyl. Yield=83%, optical purity=96%, m.p.=202°–204° C., and $[\alpha]_D^{24}=+35.0°$ (c, 0.500, THF).

Example 8

The same procedure as in Examples 5 and 7 was effected except that (1R,2R)-(−)-1,2-cyclohexanediamine used in Example 5 was replaced with (1S,2S)-(+)-1,2-cyclohexanediamine of $[\alpha]_D^{24}=+35°$ (c 4.00, $H_2O$), thereby obtaining (S)-(−)-2,2'-dihyroxy-1,1'-binaphthyl. Yield=75% (to the half amount of dl-2,2'-dihydroxy-1,1'-binaphthyl), optical purity 96%, m.p.=202°–204° C. and $[\alpha]_D^{24}=-35.1°$ (c, 0.504, THF).

Example 9

10.0 g (47.1 mmol) of (1R,2R)-(+)-1,2-diphenylethylenediamine of $[\alpha]_D^{24}=+103°$ (c 1.00, MeOH) and 13.5 g (47.1 mmol) of dl-2,2'-dihydroxy-1,1'-binaphthyl were added to 5 ml of benzene, and then heated/dissolved therein, and the solution was cooled to room temperature. Afterward, the precipitated crystals were collected by filtration and then recrystallized from 20 ml of benzene 4 times to obtain 7.97 g of a purified complex. Its yield was 68% (to the half amount of dl-2,2'-dihydroxy-1,1'-binaphthyl), and physical properties of the product are as follows.

m.p.: 55°–57° C.

$[\alpha]_D^{24}=+14.8°$ (c 0.500, benzene)

IR ($cm^{-1}$, KBr disk): 3520, 3420, 3390, 3300, 3600–2000, 1615, 1590, 1505

$^1$H-NMR ($CDCl_3$) δ: 3.20 (s, 6H), 3.78 (s, 2H) 6.8–8.1 (m, 12H), 7.33 (s, 10H)

Example 10

150 ml of 0.1M hydrochloric acid was added under ice cooling to 2.12 g (4.25 mmol) of (R)-(+)-2,2'-dihydroxy-1, 1'-binaphthyl• (1R,2R)-(+)-1,2-diphenylethylenediamine complex obtained in Example 9, followed by stirring for 30 minutes. The precipitated white solid was washed with water, and then dried under reduced pressure to obtain 1.19 g (4.16 mmol) of (R)-(+)-2,2'-dihydroxy-1,1'-binaphthyl. Yield=66% (to the half amount of dl-2,2'-dihydroxy-1,1'-binaphthyl), m.p.=202°–203° C., and $[\alpha]_D^{24}=+30.1°$ (c 0.500, THF).

Example 11

The same procedure as in Example 9 (however, the purification of crystals by recrystallization was omitted) and Example 10 was effected except that (1R,2R)-(+)-1,2-diphenylethylenediamine used in Example 9 was replaced with (1S,2S)-(−)-1,2-diphenylethylenediamine of $[\alpha]_D^{24}=-103°$ (c 1.00, MeOH) to obtain (S)-(−)-2,2'-dihydroxy-1,1'-binaphthyl. Yield=123% (to the half amount of dl-2,2'-dihydroxy-1,1'-binaphthyl), m.p.=202°–204° C., and $[\alpha]_D^{24}=-20.8°$ (c 0.504, THF).

Example 12

1.00 g (4.7 mmol) of (1R,2R)-(+)-1,2-diphenylethylenediamine of $[\alpha]_D^{20}=+103°$ (c 1.00, MeOH) and 2.09 g (4.71 mmol) of dl-6,6'-dibromo-2,2'-dihydroxy-1,1'-binaphthyl were added to 4 ml of ether and then heated and stirred, and the solution was cooled to room temperature. Afterward, the precipitated crystals were collected by filtration and then recrystallized from 3 ml of ether once to obtain 0.836 g of (1R,2R)-(+)-1,2-diphenylethylenediamine•(R)-(−)-6,6 -dibromo-2,2'-dihydroxy-1,1'-binaphthyl. Physical properties of the product are as follows.

m.p.: 101°–104° C.

IR (cm$^{-1}$, KBr disk): 3460, 3400, 3320, 3600–2400, 1610, 1590, 1500, 820, 700

$^1$H-NMR (CD$_3$SOCD$_3$) δ: 3.4 (brs, 6H), 3.7 (s, 2H), 6.7–8.0 (m, 20H)

3 ml of ethanol and 10 ml of 1M hydrochloric acid were added to 0.836 g (1.27 mmol) of the above-mentioned crystals under ice cooling, followed by stirring for 30 minutes. The precipitated crystals were collected by filtration and then dried in vacuo to obtain 0.410 g (0.923 mmol) of (R)-(−)-6,6'-dibromo-2,2'-dihydroxy-1,1'-binaphthyl. Yield=39% (to the half amount of dl-6,6'-dibromo-2,2'-dihydroxy-1,1'-binaphthyl), m.p.=109°–114° C., and $[\alpha]_{578}^{24}$=−131.7° (c 0.501, CH$_2$Cl$_2$) [literature value: $[\alpha]_{578}^{24}$=−129° (c 1.0, CH$_2$Cl$_2$)].

Example 13

2.00 g (17.5 mmol) of (1R,2R)-(−)-1,2-cyclohexanediamine of $[\alpha]_D^{20}$=−36.7° (c 4.14, H$_2$O) and 4.00 g (17.6 mmol) of dl-1-hydroxy-2-hydroxyimino-1,2-diphenylethane were added to 10 ml of benzene and then heated and stirred, and the solution was cooled to room temperature. Afterward, the precipitated crystals were collected by filtration and then recrystallized from 30 ml of benzene twice to obtain 2.30 g of (1R,2R)-(−)-1,2-cyclohexanediamine• (R)-(−)-(E)-1-hydroxy-2-hydroxyimino-1,2-diphenylethane. Physical properties of the product are as follows.

m.p.: 85°–100° C.

IR (cm$^{-1}$, KBr disk): 3500, 3400, 3360, 3330, 3300, 3250, 3600–2400, 960, 710

$^1$H-NMR (CDCl$_3$–CD$_3$SOCD$_3$) δ: 0.7–2.7 (m, 10H), 2.7–4.6 (brs, 6H), 5.6 (s, 1H), 7.2 (s, 10H).

2 ml of ethanol and 10 ml of 1M hydrochloric acid were added to 1.00 g (2.93 mmol) of the above-mentioned crystals under ice cooling, followed by stirring for 30 minutes. The precipitated crystals were collected by filtration and then dried in vacuo to obtain 0.483 g (2.13 mmol) of (R)-(−)-(E)-1-hydroxy-2-hydroxyimino-1,2-diphenylethane. Yield=56% (to the half amount of dl-1-hydroxy-2-dihydroxyimino-1,2-diphenylethane), and $[\alpha]_D^{24}$=−5.12° (c 0.508, CHCl$_3$) [literature value: $[\alpha]_D^{24}$=−3.2° (c 0.5, CHCl$_3$)].

$^1$H-NMR (CD$_3$COCD$_3$–CD$_3$SOCD$_3$) δ: 4.8 (s, 1H), 5.6 (s, 1H), 7.2 (s, 10H), 10.0 (s, 1H).

Example 14

0.934 g (4.40 mmol) of (1S,2S)-(−)-1,2-diphenylethylenediamine of $[\alpha]_D^{20}$=−103.1° (c 1.00, MeOH) and 1.00 g (4.40 mmol) of dl-1-hydroxy-2-hydroxyimino-1,2-diphenylethane were added to 3 ml of benzene and then heated and stirred, and the solution was cooled to room temperature. Afterward, the precipitated crystals were collected by filtration and then recrystallized from 2 ml of benzene once to obtain 0.250 g of (1S,2S)-(−)-1,2-diphenylethylenediamine• 1-hydroxy-2-hydroxyimino-1,2-diphenylethane. Physical properties of the product are as follows.

m.p.: 152°–155° C.

$[\alpha]_D^{24}$=−8.98° (c 1.00, CHCl$_3$)

$^1$H-NMR (CDCl$_3$) δ: 4.2 (s, 2H), 5.6 (s, 1H), 7.3 (s, 20H)

2 ml of ethanol and 20 ml of 1M hydrochloric acid were added to 0.250 g (0.569 mmol) of the above-mentioned crystals under ice cooling, followed by stirring for 30 minutes. The precipitated crystals were collected by filtration and then dried in vacuo to obtain 0.129 g (0.569 mmol) of (S)-(+)-1-hydroxy-2-hydroxyimino-1,2-diphenylethane. Yield=26% (to the half amount of dl-1-hydroxy-2-dihydroxyimino-1,2-diphenylethane), and $[\alpha]_D^{24}$=+7.95° (c 1.01, CHCl$_3$).

$^1$H-NMR (CD$_3$SOCD$_3$) δ: 3.3 (s, 1.5H), 5.5 (s, 0.5H), 5.9 (brs, 0.5H), 7.20 (s, 5H), 7.25 (s, 5H), 10.7 (s, 0.5H).

Example 15

The same procedure as in Example 1 was effected except that some of conditions were changed as follows.

1.28 g (11.2 mmol) of (1R,2R)-(−)-1,2-cyclohexanediamine of $[\alpha]_D^{20}$=−36.7° (c 4.14, H$_2$O) and 1.00 g (11.1 mmol) of dl-threo-2,3-butanediol were added to 2 ml of benzene and then heated/dissolved therein, and the solution was cooled to room temperature. Afterward, the precipitated crystals were collected by filtration to obtain 0.294 g of (1R,2R)-(−)-1,2-cyclohexanediamine•(2R,3R)-(−)-2,3-butanediol complex. The thus obtained crystals were then dissolved in ethanol, and the solution was passed through a silica gel short column and then concentrated to obtain 0.0851 g (0.944 mmol) of (2R,3R)-(−)-2,3-butanediol.

Yield=17% (to the half amount of dl-threo-2,3-butanediol), and $[\alpha]_D^{23}$=−9.16° (c 1.09, acetone).

Example 16

A filtrate obtained at the time of the filtration in Example 15 was concentrated to form a residue, and this residue was dissolved in ethanol, passed through a silica gel short column, and then concentrated to obtain 0.915 g (10.2 mmol) of (2S,3S)-(+)-2,3-butanediol.

Yield=92% (to the total amount of dl-threo-2,3-butanediol), and $[\alpha]_D^{23}$=+0.84° (c 1.10, acetone).

Example 17

The same procedure as in Example 2 was effected except that some of conditions were changed as follows.

2.00 g (17.5 mmol) of (1R,2R)-(−)-1,2-cyclohexanediamine of $[\alpha]_D^{20}$=−36.7° (c 4.14, H$_2$O) and 1.97 g (17.0 mmol) of dl-trans-1,2-cyclohexanediol were added to 5 ml of benzene and then heated/dissolved therein, and the solution was cooled to room temperature. Afterward, the precipitated crystals were collected by filtration and then recrystallized from 5 ml of benzene to obtain 1.21 g (5.25 mmol) of (1R,2R)-(−)-1,2-cyclohexanediamine•(1R,2R)-(−)-1,2-cyclohexanediol complex. The thus obtained crystals were dissolved in ethanol, and the solution was passed through a silica gel short column and then concentrated to obtain 0.660 g (5.25 mmol) of (1R,2R)-(−)-1,2-cyclohexanediol.

Yield=62% (to the half amount of dl-trans-1,2-cyclohexanediol), and $[\alpha]_D^{24}$=−31.3° (c 0.02, H$_2$O).

Example 18

The crystals in Example 17 were joined to a filtrate obtained at the time of the recrystallization in Example 17, and the mixture was then concentrated to form a residue. This residue was dissolved in ethanol, passed through a silica gel short column, and then concentrated to obtain 1.36 g (11.7 mmol) of (1S,2S)-(+)-1,2-cyclohexanediol.

Yield=69% (to the total amount of dl-trans-1,2-cyclohexanediol), and $[\alpha]_D^{23}$=+14°–0° (c 0.02, H$_2$O).

Example 19

The same procedure as in Example 3 was effected except that some of conditions were changed as follows.

0.874 g (7.65 mmol) of (1R,2R)-(–)-1,2-cyclohexanediamine of $[\alpha]_D^{20}$=–36°–7° (c 4.14, H$_2$O) and 1.63 g (7.61 mmol) of dl-threo-1,2-diphenyl-1,2-ethanediol were added to 7 ml of benzene and then heated/dissolved therein, and the solution was cooled to room temperature. Afterward, the precipitated crystals were collected by filtration and then recrystallized from 5 ml of benzene to obtain 0.765 g (2.33 mmol) of (1R,2R)-(–)-1,2-cyclohexanediamine• (1S,2S)-(–)-1,2-diphenyl-1,2-ethanediol complex. 1 ml of ethanol and 10 ml of 1M hydrochloric acid were added to the above-mentioned crystals under ice cooling, followed by stirring for 30 minutes. The solution was extracted with methylene chloride, washed with water, dried over anhydrous sodium sulfate, and then concentrated to obtain 0.499 g (2.33 mmol) of (1S,2S)-(–)-1,2-diphenyl-1,2-ethanediol.

Yield=61% (to the half amount of dl-threo-1,2-diphenyl-1,2-ethanediol), and $[\alpha]_D^{24}$=–90.4° (c 2.50, EtOH).

Example 20

The crystals in Example 19 were joined to a filtrate obtained at the time of the recrystallization in Example 19, and the mixture was then concentrated to form a residue. 3 ml of methanol and 30 ml of 1M hydrochloric acid were added to the thus formed residue under ice cooling, followed by stirring for 30 minutes. The solution was extracted with methylene chloride, washed with water, dried over anhydrous sodium sulfate, and then concentrated to obtain 1.13 g (5.27 mmol) of (1R,2R)-(+)-1,2-diphenyl-1,2-ethanediol.

Yield=69% (to the total amount of dl-threo-1,2-diphenyl-1,2-ethanediol), and $[\alpha]_D^{24}$=+40.0° (c 2.50, EtOH).

Example 21

The same procedure as in Example 8 was effected except that some of conditions were changed as follows.

1.00 g (8.76 mmol) of (1R,2R)-(–)-1,2-cyclohexanediamine of $[\alpha]_D^{20}$=–36.7° (c 4.14, H$_2$O) and 2.51 g (8.77 mmol) of dl-2,2'-dihydroxy-1,1'-binaphthyl were added to 25 ml of toluene and then heated/dissolved therein, and the solution was cooled to room temperature. Afterward, the precipitated crystals were collected by filtration and then recrystallized from 25 ml of toluene to obtain 1.73 g (3.51 mmol) of (1R,2R)-(–)-1,2-cyclohexanediamine• (R)-(+)-2,2'-dihydroxy-1,1'-binaphthyl•toluene (1:1:1) complex. 2 ml of methanol and 20 ml of 1M hydrochloric acid were added to the above-mentioned crystals under ice cooling, followed by stirring for 30 minutes. The precipitated crystals were filtered, washed with water, and then dried in vacuo to obtain 1.00 g (3.50 mmol) of (R)-(+)-2,2'-dihydroxy-1,1'-binaphthyl.

Yield=80% (to the half amount of dl-2,2'-di-hydroxy-1,1'-binaphthyl), and $[\alpha]_D^{24}$=+35.0° (c 0.50, THF).

Example 22

The crystals in Example 21 were joined to a filtrate obtained at the time of the recrystallization in Example 21, and the mixture was then concentrated to form a residue. 3 ml of methanol and 30 ml of 1M hydrochloric acid were added to the thus formed residue under ice cooling, followed by stirring for 30 minutes. The precipitated crystals were filtered, washed with water, and then dried in vacuo to obtain 1.51 g (5.26 mmol) of (S)-(–)-2,2'-dihydroxy-1,1'-binaphthyl.

Yield=60% (to the total amount of dl-2,2'-dihydroxy-1,1'-binaphthyl), and $[\alpha]_D^{24}$=–23.3° (c 0.50, THF).

Example 23

1.00 g (8.76 mmol) of dl-1,2-cyclohexanediamine and 2.51 g (8.77 mmol) of (R)-(+)-2,2'-dihydroxy-1,1'-binaphthyl of $[\alpha]_D^{24}$=+35.5° (c 0.50, THF) were added to 25 ml of toluene and then heated/dissolved therein, and the solution was cooled to room temperature. Afterward, the precipitated crystals were collected by filtration and then recrystallized from 25 ml of toluene to obtain 1.82 g (3.69 mmol) of (1R,2R)-(–)-1,2-cyclohexanediamine• (R)-(+)-2,2'-dihydroxy-1,1'-binaphthyl•toluene (1:1:1) complex. The crystals of this complex were thermally decomposed at 180° C. under a reduced pressure of 10 mmHg, thereby obtaining 0.40 g (3.50 mmol) of (1R,2R)-(–)-1,2-cyclohexanediamine as a distillate.

Yield=80% (to the half amount of dl-1,2-cyclohexanediamine), and $[\alpha]_D^{20}$=–36.3° (c 4.14, H$_2$O).

Example 24

The crystals in Example 23 were joined to a filtrate obtained at the time of the recrystallization in Example 23, and the mixture was then concentrated to form a residue. This residue was thermally decomposed at 180° C. under a reduced pressure of 10 mmHg to obtain 0.52 g (4.55 mmol) of (1S,2S)-(+)-1,2-cyclohexanediamine as a distillate.

Yield=52% (to the total amount of dl-1,2-cyclohexanediamine), and $[\alpha]_D^{20}$=+26.4° (c 4.14, H$_2$O).

Example 25

1.00 g of (R)-(+)-2,2'-dihydroxy-1,1'-binaphthyl having an optical purity of 100% ee (HPLC: Chiralpak OT made by Daisel Ltd.; the same shall apply hereinafter) was heated/melted at 220° C. for 10 minutes in a nitrogen atmosphere. After cooling, 2,2'-dihydroxy-1,1'-binaphthyl having an optical purity of 0% ee was obtained.

Example 26

2.65 g (9.26 mmol) of (R)-(+)-2,2'-dihydroxy-1,1'-binaphthyl having an optical purity of 100% ee and 1.00 g (9.25 mmol) of o-phenylenediamine were heated under reflux for 2 hours in 5 ml of toluene in a nitrogen atmosphere and then cooled to precipitate crystals. Afterward, 3 ml of ethanol and 30 ml of 1M hydrochloric acid were added to the thus precipitated crystals under ice cooling, followed by stirring for 30 minutes. The precipitated crystals were filtered and then dried in vacuo to obtain 2.52 g (8.80 mmol) of 2,2'-dihydroxy-1,1'-binaphthyl having an optical purity of 100% ee. Its yield was 95%.

Example 27

4.76 g (16.6 mmol) of (R)-(+)-2,2'-dihydroxy-1,1'-binaphthyl having an optical purity of 100% ee and 1.00 g (16.6 mmol) of ethylenediamine were heated under reflux for 20 hours in 20 ml of toluene in a nitrogen atmosphere and then cooled to precipitate crystals. Afterward, 3 ml of ethanol and 30 ml of 1M hydrochloric acid were added to the thus precipitated crystals under ice cooling, followed by stirring for 30 minutes. The precipitated crystals were filtered and then dried in vacuo to obtain 4.09 g (14.3 mmol) of 2,2'-dihydroxy-1,1'-binaphthyl having an optical purity of 0% ee. Its yield was 86%.

Example 28

A mixture of 1.00 g (8.76 mmol) of dl-1,2-cyclohexanediamine and 2.51 g (8.77 mmol) of (R)-(+)-2,2'-dihydroxy-1,1'-binaphthyl having an optical purity of 100% ee was heated/melted at 170° C. for 2 hours and then cooled. Afterward, 3 ml of ethanol and 30 ml of 1M hydrochloric acid were added thereto, followed by stirring for 30 minutes. The precipitated crystals were filtered and then dried in vacuo to obtain 2.46 g (8.70 mmol) of 2,2'-dihydroxy-1,1'-binaphthyl having an optical purity of 0% ee. Its yield was 99%.

Example 29

10.0 g (47.1 mmol) of (1R,2R)-(+)-1,2-diphenylethylenediamine of $[\alpha]_D^{20}=+103°$ (c 1.00, MeOH) and 13.5 g (47.1 mmol) of dl-2,2'-dihydroxy-1,1'-binaphthyl were added to 30 ml of benzene in a nitrogen atmosphere, and the solution was then heated and stirred. Afterward, the solution was cooled to room temperature, and the precipitated crystals were collected by filtration. The resultant filtrate was directly heated under reflux for 40 hours and then cooled to room temperature, and the precipitated crystals were collected by filtration. The operation of refluxing and crystallizing the filtrate was repeated 5 times, and the resultant crystals were joined and recrystallization was then carried out 3 times, thereby obtaining (1R,2R)-(+)-1,2-diphenylethylenediamine•(R)-(+)-2,2'-dihydroxy-1,1-binaphthyl complex. Physical properties of the product are as follows.

m.p.: 55°–57° C.

IR (cm$^{-1}$, KBr disk): 3520, 3420, 3390, 3300, 3600–2000, 1615, 1590, 1505

$^1$H-NMR (CDCl$_3$) δ: 3.2 (s, 6H), 3.8 (s, 2H), 6.8–8.1 (m, 12H), 7.33 (s, 10H)

Afterward, 30 ml of ethanol and 300 ml of 1M hydrochloric acid were added to the above-mentioned crystals under ice cooling, followed by stirring for 30 minutes. The precipitated crystals were filtered and then dried in vacuo to obtain 12.3 g (42.9 mmol) of (R)-(+)-2,2'-dihydroxy-1,1'-binaphthyl. Yield=91% (to the total amount of dl-2,2'-dihyroxy-1,1-binaphthyl), optical purity=97% ee (HPLC), and m.p.=202°–203° C.

Example 30

100 g (876 mmol) of (1R,2R)-(−)-1,2-cyclohexanediamine of $[\alpha]_D^{20}=-36.7°$ (c 4.14, H$_2$O) and 251 g (877 mmol) of dl-2,2'-dihydroxy-1,1'-binaphthyl were added to 300 ml of toluene in a nitrogen atmosphere, and the solution was then heated and stirred. Afterward, the solution was cooled to room temperature, and the precipitated crystals were collected by filtration. The resultant filtrate was directly heated under reflux for 15 hours and then cooled to room temperature, and the precipitated crystals were collected by filtration. The operation of refluxing and crystallizing the filtrate was repeated 4 times, and the obtained crystals were joined and recrystallization was then carried out from toluene twice, thereby obtaining 388 g of (1R,2R)-(−)-1,2-cyclohexanediamine• (R)-(+)-2,2'-dihydroxy-1,1'-binaphthyl•toluene (1:1:1) complex. Physical properties of the product are as follows.

m.p.: 150°–155° C.

IR (cm$^{-1}$, KBr disk): 3450, 3380, 3300, 3060, 1620, 1600, 1515, 820, 745

$^1$H-NMR (CDCl$_3$) δ: 1.0–2.0 (m, 8H), 3.6 (s, 8H), 7.1–8.3 (m, 12H), 7.4 (s, 12H)

Afterward, 400 ml of methanol and 4000 ml of 1M hydrochloric acid were added to 388 g (788 mmol) of the above-mentioned crystals under ice cooling, followed by stirring for 30 minutes. The precipitated crystals were filtered and then dried in vacuo to obtain 221 g (772 mmol) of (R)-(+)-2,2'-dihydroxy-1,1'-binaphthyl. Yield=88% (to the total amount of dl-2,2'-dihyroxy-1,1-binaphthyl), optical purity=100% ee (HPLC), and m.p.=202°–203° C.

Example 31

100 g (876 mmol) of (1S,2S)-(+)-1,2-cyclohexanediamine of $[\alpha]_D^{20}=+36.7°$ (c 4.14, H$_2$O) and 251 g (877 mmol) of dl-2,2'-dihydroxy-1,1'-binaphthyl were added to 300 ml of toluene in a nitrogen atmosphere, and the solution was then heated and stirred. Afterward, the solution was cooled to room temperature, and the precipitated crystals were collected by filtration. The resultant filtrate was directly heated under reflux for 15 hours and then cooled to room temperature, and the precipitated crystals were collected by filtration. The operation of refluxing and crystallizing the filtrate was repeated 4 times, and the obtained crystals were joined and recrystallized from toluene twice, thereby obtaining 392 g of (1S,2S)-(+)-1,2-cyclohexanediamine•(S)-(−)-2,2'-dihydroxy-1,1'-binaphthyl• toluene (1:1:1) complex. Physical properties of the product are as follows.

m.p.: 150°–155° C.

IR (cm$^{-1}$, KBr disk): 3450, 3380, 3300, 3060, 1620, 1600, 1515, 820, 745

$^1$H-NMR (CDCl$_3$) δ: 1.0–2.0 (m, 8H), 3.6 (s, 8H), 7.1–8.3 (m, 12H), 7.4 (s, 12H)

Afterward, 400 ml of methanol and 4000 ml of 1M hydrochloric acid were added to 392 g (796 mmol) of the above-mentioned crystals under ice cooling, followed by stirring for 30 minutes. The precipitated crystals were filtered and then dried in vacuo to obtain 223 g (780 mmol) of (S)-(−)-2,2'-dihydroxy-1,1'-binaphthyl. Yield=89% (to the total amount of dl-2,2'-dihyroxy-1,1-binaphthyl), optical purity=100% ee (HPLC), and m.p.=202°–203° C.

Example 32

100 g (876 mmol) of (1R,2R)-(−)-1,2-cyclohexanediamine of $[\alpha]_D^{20}=-36.7°$ (c 4.14, H$_2$O) and 251 g (877 mmol) of (S)-(−)-2,2'-dihydroxy-1,1'-binaphthyl having an optical purity of 100% ee (HPLC) were added to 300 ml of toluene in a nitrogen atmosphere, and the solution was then heated and stirred for 15 hours. Afterward, the solution was cooled to room temperature, and the precipitated crystals were collected by filtration. The resultant filtrate was directly heated under reflux for 15 hours and then cooled to room temperature, and the precipitated crystals were collected by filtration. The operation of refluxing and crystallizing the filtrate was repeated 4 times, and the obtained crystals were joined and the recrystallized from toluene twice, thereby obtaining 370 g of (1R,2R)-(−)-1,2-cyclohexanediamine• (R)-(+)-2,2'-dihydroxy-1,1'-binaphthyl•toluene (1:1:1) complex.

Afterward, 400 ml of methanol and 4000 ml of 1M hydrochloric acid were added to 370 g (751 mmol) of the thus obtained crystals under ice cooling, followed by stirring for 30 minutes. The precipitated crystals were filtered and then dried in vacuo to obtain 211 g (737 mmol) of (R)-(+)-2,2'-dihydroxy-1,1'-binaphthyl. Yield=84% (to the total amount of (S)-(−)-2,2'-dihyroxy-1,1'-binaphthyl), optical purity=100% ee (HPLC), and m.p.=202°–203° C.

Example 33

100 g (876 mmol) of (1R,2R)-(−)-1,2-cyclohexanediamine of $[\alpha]_D^{20}=-36.7°$ (c 4.14, $H_2O$) and 251 g (877 mmol) of (S)-(−)-2,2'-dihydroxy-1,1'-binaphthyl having an optical purity of 100% ee (HPLC) were added to 300 ml of p-xylene in a nitrogen atmosphere, and the solution was then heated and stirred for 10 hours. Afterward, the solution was cooled to room temperature, and the precipitated crystals were collected by filtration. The resultant filtrate was directly heated under reflux for 10 hours and then cooled to room temperature, and the precipitated crystals were collected by filtration. The operation of refluxing and crystallizing the filtrate was repeated 4 times, and the obtained crystals were joined and then recrystallized from p-xylene 5 times, thereby obtaining (1R,2R)-(−)-1,2-cyclohexanediamine•(R)-(+)-2,2'-dihydroxy-1,1'-binaphthyl•xylene complex.

Afterward, 400 ml of methanol and 4000 ml of 1M hydrochloric acid were added to the thus obtained crystals under ice cooling, followed by stirring for 30 minutes. The precipitated crystals were filtered and then dried in vacuo to obtain 209 g (730 mmol) of (R)(+)-2,2'-dihydroxy-1,1'-binaphthyl. Yield=83% (to the total amount of (S)-(−)-2,2'-dihyroxy-1,1'-binaphthyl), optical purity=100% ee (HPLC), and m.p.=202°–203° C.

Example 34

4.42 g (38.7 mmol) of (1R,2R)-(−)-1,2-cyclohexanediamine of $[\alpha]_D^{20}=-36.7°$ (c 4.14, $H_2O$) and 17.2 g (38.7 mmol) of dl-6,6'-dibromo-2,2'-dihydroxy-1,1'-binaphthyl were added to 170 ml of p-xylene in a nitrogen atmosphere, and the solution was then heated and stirred. Afterward, the solution Was cooled to room temperature, and the precipitated crystals were collected by filtration. The resultant filtrate was directly heated under reflux for 24 hours and then cooled to room temperature, and the precipitated crystals were collected by filtration. The operation of refluxing and crystallizing the filtrate was repeated 4 times, and the obtained crystals were joined and then recrystallized from xylene 5 times, thereby obtaining a crystalline complex comprising (1R,2R)-(−)-1,2-cyclohexanediamine and (R)-(−)-6,6'-dibromo-2,2'-dihydroxy-1,1'-binaphthyl.

Afterward, 20 ml of ethanol and 200 ml of 1M hydrochloric acid were added to the thus obtained crystals under ice cooling, followed by stirring for 30 minutes. The precipitated crystals were filtered and then dried in vacuo to obtain 15.8 g (35.6 mmol) of (R)-(−)-6,6' -dibromo-2,2'-dihydroxy-1,1'-binaphthyl. Yield=92% (to the total amount of dl-6,6'-dibromo-2,2'-dihydroxy-1,1'-binaphthyl) and optical purity=100% ee (HPLC).

What is claimed is:

1. A method for optically resolving a bifunctional compound, which comprises the steps of:

reacting an optically active bifunctional resolving reagent with said bifunctional compound to form a liquid material, precipitating first crystals from said liquid material, separating said first crystals from said liquid material,
 (a) treating said first crystals thus separated with an acidic material, a basic material, or both a basic material and an acidic material,
 (b) heating the separated liquid material, cooling it or allowing it to stand, whereby second crystals are formed, separating said second crystals from the liquid material, and then treating the separated second crystals with an acidic material, a basic material, or both a basic material and an acidic material, and collecting only one enantiomer of a pair of enantiomers of an optically active bifunctional compound from said steps (a) and (b), wherein said bifunctional compound is a compound selected from the group consisting of dihydroxy compounds, hydroxyoxime compound and diamino compounds, and said optically active bifunctional resolving reagent is an optically active diamino compound or an optically active dihydroxy compound.

2. The method according to claim 1 wherein said bifunctional compound is a binaphthol represented by the formula (A)

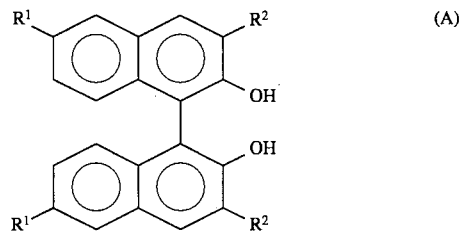

wherein $R^1$ is H, Br or OH, and $R^2$ is H, Br, OH, $CH_3$, $CO_2H$, $CO_2CH_3$, $CO_2CH_2CH_3$ or $CH_2OH$, and said optically active bifunctional resolving reagent is an optically active diamine.

3. The method according to claim 1 wherein in the step (a) said first crystals thus separated are treated with an acidic material, and in the step (b) said second crystals are treated with an acidic material, said bifunctional compound is a binaphthol selected from the group consisting of 2,2'-dihydroxy-1,1'-binaphthyl and 6,6,-dibromo-2,2'-dihydroxy-1,1'-binaphthyl, and said optically active bifunctional resolving reagent is an optically active diamino compound selected from the group consisting of 1,2-diphenylethylenediamine and 1,2-cyclohexanediamine.

4. The method according to claim 1 wherein the step of precipitating crystals comprises adding a solvent for said crystals to said liquid material, heating the resultant mixture to dissolve solids therein, and then cooling the mixture.

5. The method according to claim 1 wherein the liquid material separated from the second crystals in step (b) is further heated and then cooled or allowed to stand, whereby third crystals are formed, the third crystals are separated from the liquid material, the separated third crystals are treated by step (a), the separated liquid material is treated by step (b), and this operation is then repeated.

* * * * *